Figure 1:
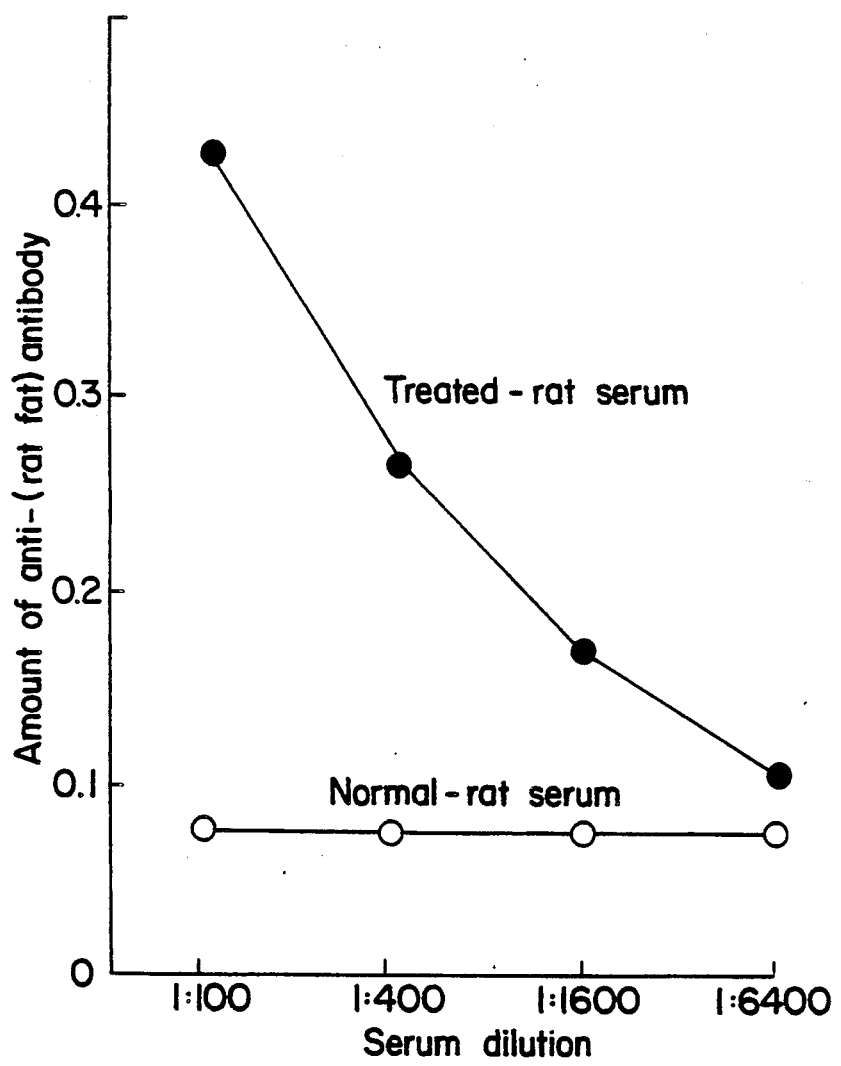

United States Patent [19]

Flint

[11] Patent Number: 5,096,706

[45] Date of Patent: Mar. 17, 1992

[54] ANTIGEN-BASED TREATMENT FOR ADIPOSITY

[75] Inventor: David J. Flint, Troon, Scotland

[73] Assignee: National Research Development Corporation, England

[21] Appl. No.: 843,790

[22] Filed: Mar. 25, 1986

[51] Int. Cl.$^5$ ............................................. A61K 39/00
[52] U.S. Cl. ........................................ 424/88; 424/89; 424/90; 424/91; 424/92; 424/574; 514/21; 530/350; 530/380
[58] Field of Search .................. 530/403, 387; 424/85, 424/88, 86, 89, 90, 93; 514/21

[56] References Cited

U.S. PATENT DOCUMENTS 4,526,716  7/1985  Stevens ............................... 530/403

FOREIGN PATENT DOCUMENTS 80819  6/1969  Luxembourg .

OTHER PUBLICATIONS

Pillion et al., J. Biol Chem. 225, (1980) pp. 9168–9176.
A. Cryer, Reprod. Nutr. Develop. 25 (1B), 159–164 (1985).
D. J. Pillion et al., J. Biol. Chem. 253, 3761–3764 (1978).
D. J. Pillion et al., J. Biol Chem. 254, 3211–3220 (1979).
R. K. Tume et al., Comp. Biochem. Physiol. 803, 127–134 (1985).
"Feedstuffs" (The Weekly Newspaper for Agribusiness), vol. 57, No. 47. pp. 1 and 23 (Nov. 1985).
Bernard Dixon in "The Guardian" (English daily newspaper), Jan. 31, 1986 p. 23.
A. Cryer et al., J. Develop. Physiol., 6, 159–176 (1984).
Coggrave et al., J. Endocrinology, 102 (Supplement), Abstract No. 41 (1984).
C. E. Futter et al., poster P4 exhibited at University of Nottingham 43rd Easter School, Sutton Bonington, 15–18 Apr. 1985.

Primary Examiner—Esther L. Kepplinger
Assistant Examiner—Jeff Kushan
Attorney, Agent, or Firm—Rosenman & Colin

[57] ABSTRACT

A method of preventing, controlling or reducing adiposity in which an animal or human subject is treated with an immunogen which is a modified or unmodified antigenic substance obtainable from adipose tissue of an individual of the same species as the subject or of a species which is closely related phylogenetically to the species of the subject or which is a modified or unmodified antiidiotypic antibody or fragment thereof to an antibody raised against said antigenic substance whereby an immune response is elicited in the subject effective to prevent, control or reduce adiposity.

7 Claims, 2 Drawing Sheets

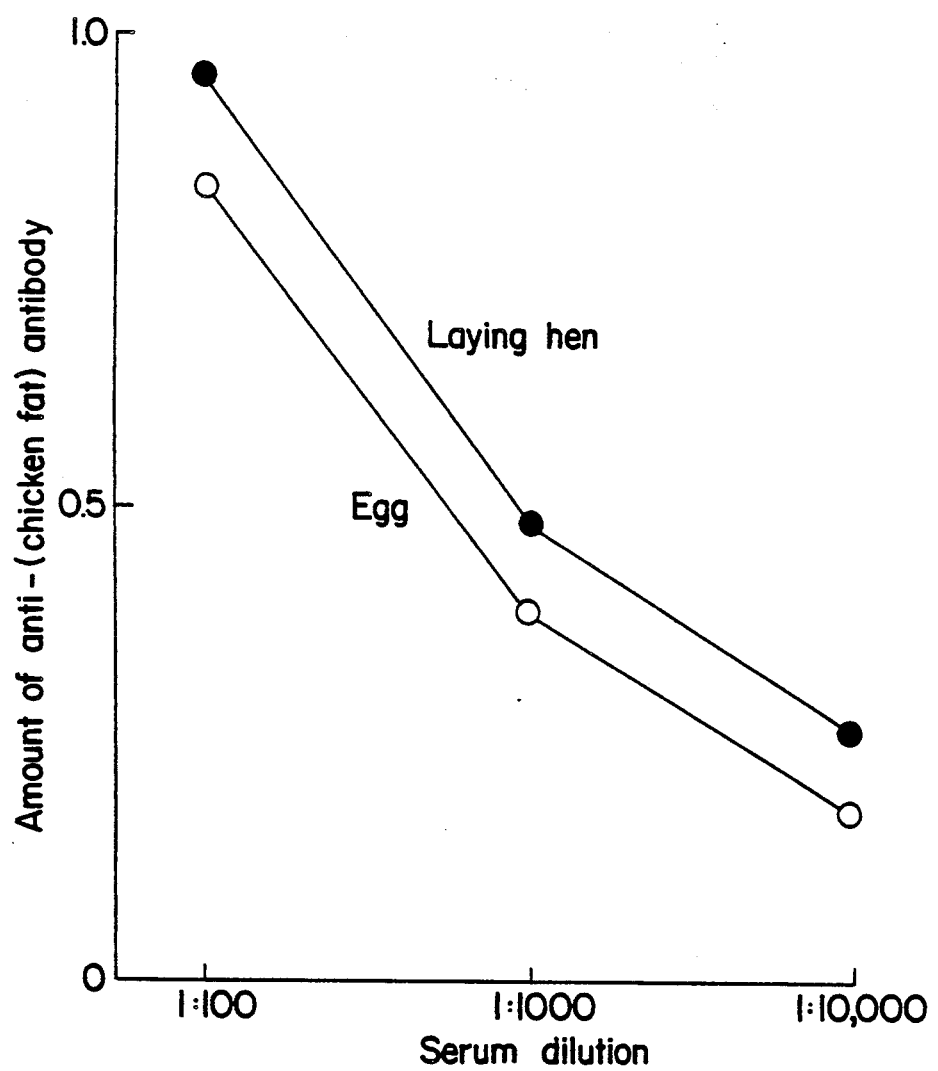

ANTIGEN-BASED TREATMENT FOR ADIPOSITY

This invention relates to the prevention, reduction and control of adiposity in non-human and human animal subjects.

In U.S. application Ser. No. 757,069 there is described a method of preventing, controlling or reducing adiposity in which an animal or human being is treated with an effective amount of an antibody to an adipocyte present respectively in the animal or human being.

Such a method of immunization, termed "passive immunication", whilst effective, is somewhat expensive and it has now been found that an alternative and relatively inexpensive immunological method gives good results.

Accordingly, the present invention comprises a method of preventing controlling or reducing adiposity in which an animal subject is treated with an immunogen which is a modified or unmodified antigenic substance obtainable from adipose tissue of an individual of the same species as the subject of a species which is closely related phylogenetically to the species of the subject or which is a modified or unmodified anti-idiotypic antibody or fragment thereof to an antibody raised against said antigenic substance whereby an immune response is elicited in the subject effective to prevent, control or reduce adiposity.

Antigenic substances useful in this method of active immunization may comprise preparations of whole adipocytes or, in preferred embodiments, adipocyte plasma membrane material, which is preferably purified for use so that the specificity of the immune response elicited is increased. The antigenic substance may comprise a single component of plasma membrane or a mixture of such components.

Fat tissue, which may originate, for example, in a parametrial, subcutaneous, mesenteric or perirenal depot or a plurality of depots, may be treated with a collagenase to yield isolated adipocytes which are lysed to liberate adipocyte plasma membrane material from which, if desired, fat cell specific antigens may be produced. A typical procedure for the production of such antigens includes passing a crude adipocyte plasma membrane preparation through an affinity column comprising, as immuno-adsorbent, purified adipocyte specific antibodies and eluting the bound antigen, suitably by use of pH change or protein-deforming agents. The adipocyte specific antibodies may be obtained from an antiserum raised by administration of antigenic substance obtained from adipose tissue present in a first species to a donor of a second species. Typically, the anti-serum is passed through an affinity column, the imuno-adsorbent of which is crude immunogen and elution yields partially purified antiserum which is usually contaminated by antibodies reactive to cell types other than the adipocyte. Passage through an affinity column comprising liver, kidney and erythrocyte membranes removes these non specific antibodies and yields purified adipocyte specific antibodies suitable for preparing the affinity column used to produce purified adipocyte specific antigen.

In a simpler, alternative procedure for producing adipocyte specific antigen, antiserum raised against immunogen obtainable from adipose tissue, for example plasma membrane material, is treated with a liver membrane immuno-adsorbent so that non specific antibodies are removed. The resultant relatively specific antiserum is used to immuno-precipitate adipocyte-specific antigens from the material used to raise the antiserum.

In order to increase the response elicited by the immunogen, the antigenic substance, anti-idiotypic antibody or fragment thereof may be modified and this is especially preferred when the antigenic substance is adipocyte plasma membrane or one or more immunogenic components thereof. Modification may take the form of cross linkage to accomplish, for example, oligomerisation or polymerisation or derivatisation such as methylation, acylation, including acetylation, dinitrophenylation, trinitrophenylation, iodination or conjugation to a carrier which is generally a peptide or is proteinaccous and capable of conferring hapten characteristics upon small molecules, such as a serum albumin e.g. human or bovine serum albumin or a human $\alpha$-globulin. Conjugation may be effected by means of glutaraldehyde or carbodiimide or heterobifunctional agent. Modification may also take the form of covalent linkage to a lipopeptide mitogen, a B- or T- cell mitogen, or to a virus or part thereof the linkage being either direct or by way of a different moiety such as a carrier of the type hereinbefore described.

A relatively increased immune response may be elicited by administration of the immunogen before, after or simultaneously with an adjuvant such as Freund's adjuvant or a different immunopotentiator.

In particularly preferred embodiments of the present invention, the non-human or human animal subject is treated with an anti-idiotypic antibody raised against immunogen obtainable from adipose tissue present in an individual of he same species or a phylogenetically closely related species as the said subject.

When antibodies are produced to an antigen, the antibodies contain within their variable (binding) region a surface which is complementary to that of the antigen and can, therefore, be considered as an anti-image of the antigen. If this first antibody (referred to as the idiotypic antibody) is then used to immunize a second animal, this second animal produces a second antibody against the first antibody. The second antibody (referred to as an anti-idiotypic antibody) will also carry binding regions which are anti-images of the binding region of the first antibody. This will in turn mean that the binding region of the second antibody will be an image of the antigen. The following procedure is suitable for carrying the invention into effect:

Approximately 100 $\mu$g of plasma membranes from fat cells of the relevant species are injected, in complete Freund's adjuvant, into mice. Repeat injections are administered on 2-5 subsequent occasions. 3-4 days after the final injection, the spleens of these mice are used to prepare lymphocytes some of which secrete antibodies to fat cell plasma membranes. These lymphocytes are fused with myeloma cells to form stable hybridomas. Clones of these hybridomas secreting the appropriate antibodies are grown in culture and the antibodies obtained from the culture medium. These antibodies (idiotypes) or fragments (FAB or (FAB)$_2$) are then injected into a second set of mice where anti-idiotypic antibodies will be produced. Spleens from these mice are fused in identical fashion to that described for the idiotypic antibodies allowing the selection of hybridoma clones secreting antibody which contains within its binding region an antigen image.

Additional information on the production of anti-idiotypic vaccines employing anti-idiotypic monoclonal antibodies is contained in European Patent Application No. Publication No. 142345A of Synbiotics Corporation. The present invention includes within its scope anti-idiotypic antibody per se and a hybridoma secreting monoclonal antibody.

Applications of the present invention include:

The immunization of lambs and calves to produce lean meat; the production of lean ewes, for example in lowland farming where excess fatness may be unnecessary and energetically expensive; the more efficient production of milk, which may have a low fat content, from lean cattle fed with concentrates; the reduction of excess abdominal fat in broiler chickens; reduction of fat and particularly subcutaneous fat in duck; the product of leaner carcasses in pigs and the reduction of reproduction problems due to obesity; the reduction of human obesity.

In an application of particular interest, a female subject is treated with immunogen during pregnancy or lactation whereby the resultant immunity is transmitted to the offspring. Laying birds for example when immunized, yield eggs with significant antibody titres.

The dosage of immunogen depends of course on both the nature of the immunogen and of the subject and can be readily established by simple trials. For guidance, however, the dosages generally lie in the range 50–250 micrograms and only rarely exceed 2 mg.

The invention is illustrated by the following Examples:

1. ACTIVE IMMUNIZATION AGAINST ADIPOSE TISSUE

A. Preparation of rat cell membranes for immunization

Parametrial, perirenal and subcutaneous adipose tissue is removed from 180–250 g female Wistar rats. The tissue is minced with scissors and incubated for 90 min at 37° in Krebs ringer phosphate buffer containing 1 mg/ml collagenase and 3 mg/ml bovine serum albumin to prepare isolated adipocytes.

The digested tissue is filtered through a nylon sieve and the isolated adipocytes washed by flotation 3× in Krebs ringer phosphate.

The washed cells are then vortexed for 60 seconds in 100 mM Tris HCl buffer pH 7.4 containing 0.25M sucrose and 20 mM EGTA ethylene glycol-bis ($\beta$-aminoethylether)-N,N,N', N'-tetracetic acid to lyse the cells and centrifuged (2000×5 min) to remove the lipid. The infranatant containing broken cell debris (including plasma membranes) is centrifuged at 13000 g for 15 min to harvest the membranes. The supernatant is discarded and the pellet resuspended in 2 ml medium, homogenised and then mixed with a Percoll-containing density gradient (Tris HCl medium containing Percoll 17.5% (v/V) medium and centrifuged at 5000×15 min. The purified plasma membranes appear at the top of the gradient and are carefully removed and harvested by centrifugation at 80000 g for 20 min. The pellet is finally resuspended in Tris HCl buffer pH 7.4, containing 0.15M NaCl, and used for immunization.

B. Production of fat cell membrane BSA conjugate

100 μg of fat cell plasma membrane (2 mg/ml) are mixed with 100 μg of bovine serum albuman (2 mg/ml). 20 μl of 0.5% glutaraldehyde is added slowly whilst stirring and is left for 30 min. The suspension is then emulsified with 200 μl of Freund's adjuvant immediately prior to injection.

C. Active immunization of rats with fat cell plasma membranes

Female Wistar rats weighing ca. 50 g are injected with 100 μg of rat fat cell plasma membranes conjugated to bovine serum albumin, as described above in Section B, in complete Freund's adjuvant administered at 2 subcutaneous sites. Control rats receive identical injections with the exception that the plasma membranes are omitted. Injections are repeated on days –and 28 using incomplete Freund's adjuvant. On days 45 and 73 treated animals receive fat cell plasma membranes (100 μg) unconjugated, whilst controls receive incomplete Freund's adjuvant. Food intakes and body weights are monitored throughout the experiment. Animals are anaesthetized with ether on days 42, 56, 84 and 112 in order that a small blood sample can be obtained, in order to assess antibody responses, as described in Section D.

A small number of animals are killed 112 days after the beginning of treatment. Parametrial, perirenal, mesenteric and subcutaneous fat depots are dissected out and dried to constant weight. In some animals a small portion of the parametrial fat depot is removed before drying and is minced and digested in collagenase as described in Section A. The diameters of 100 cells from each depot are measured using a light microscope in order to calculate the mean cell volume. From the dry weight of the tissue and assuming a density for lipid of 0.91 g/ml, the total number of fat cells in these depots is calculated using the formula;

$$\text{Cell number} = \frac{\text{cell weight}}{0.91} \times \frac{10^9}{\text{mean cell volume (picolitres)}}$$

D. Assessment of antibody titres by enzyme-linked immunoassay (EIA)

Antibody titres are determined by enzyme-immunoassay (EIA). Briefly, 1 μg of plasma membranes in 100 μl at 0.01M. sodium phosphate, 0.15M Nacl buffer pH 7.4 (PBS) are absorbed passively on 96-well plates (Flow Laboratores, Irvine, Scotland, UK) by incubation overnight at 4° C. The plates are then aspirated, washed 3 times in PBS saline pH 7.4 containing 0.05% Tween 80 (PBS:Tween) and left for 1 hour full of PBS:Tween to block non-specific absorption sites. Various dilutions of antiserium or normal serum are added to the plates in a volume of 100 μof PBS:Tween. After 2 hours at room temperature, the sera are removed and the plates washed 3× with PBS:Tween. 100 μl of a 1:600 dilution of anti-sheet/goat alkaline phosphatase conjugate (Sigma, Pool, Dorset) is added to the plates and incubation continued for a further 2 hours. The plate is washed again and 250 μl of phosphatase substrate (Sigma, Poole, Dorset) is added (1 mg/ml substrate in 0.1M Glycine, 1 mM ZnCl$_1$ 1 mM MgCl$_2$ pH 10.4) and the plates incubated in the dark. After 15–30 min the reaction is terminated by the addition of 50 μl of 0.5N NaOH and the colour development determined by reading the optical density at 405 nm in a Multiskan spectrophotometer (Flow Laboratories, Irvine, UK).

Effects of treatment on body fat depots are illustrated in Table 1 and antibody titres in treated animals are illustrated in FIG. 1.

EXAMPLE 2

Active immunization against fat cell plasma membrane in laying hens and detection of antibodies to fat cells in their eggs The hens used are of a commercial strain bred for egg-laying performance (Isa Warren), and are fed ad libitum on a standard commercial-type diet. The hens are 24–26 weeks of age at the start of the immunization procedure and therefore at their peak of lay.

Immunization is started by injecting each of six hens with 0.2 mg purified chicken fat cell membrane protein cross-linked to bovine serum albumin and emulsified in Freund's complete adjuvant. Injections are made into the breast muscle at multiple sites. This procedure is repeated at 2–3 week intervals using Freund's incomplete adjuvant, twice with the same antigen as before and twice with 0.2 mg purified fat cell membrane protein alone.

Antibody titres are measured (by EIA) in plasma and yolk prepared from blood and eggs collected approximately 2 weeks after the final immunisation and compared to those in plasma and yolk from untreated hens. The results are shown in FIG. 2. Plasma is prepared by centrifuging blood withdrawn from the wing-vein at 1000 g for 10 min. EDTA is used as anti-coagulant. Antibody in yolk is measured after removal of yolk lipoproteins with dextran sulphate. 1 ml aliquots of yolk are mixed with 7 ml 0.2% dextran sulphate (MW 40000) in 100 mM $CaCl_1$/10 mM Tris. HCl, pH 7.4 and precipitated lipoproteins removed by centrifugation at 1000 g for 10 min. Any floating precipitate is removed by filtration of the supernatant through sintered glass.

TABLE 1

RATS ACTIVELY IMMUNIZED WITH RAT FAT CELL MEMBRANES CONJUGATED TO BSA DRY WEIGHTS DISSECTED FAT

|  | Control | Treated |
| --- | --- | --- |
| Corrected body weight (g) | 312 ± 10 | 287 ± 8* |
| Fat Depot weight (g) |  |  |
| Subcutaneous 1 | 6.5 ± 0.9 | 4.7 ± 0.3* |
| Subcutaneous 2 | 3.2 ± 0.2 | 2.1 ± 0.2 |
| Parametrial | 12.1 ± 1.2 | 9.6 ± 0.7 |
| Perirenal | 6.0 ± 0.8 | 4.7 ± 0.6* |
| Mesenteric | 6.8 ± 0.9 | 4.7 ± 0.7* |
| Total dissected fat (g) | 34.8 ± 4.0 | 25.8 ± 2.4* |

TABLE 1-continued

RATS ACTIVELY IMMUNIZED WITH RAT FAT CELL MEMBRANES CONJUGATED TO BSA DRY WEIGHTS DISSECTED FAT

|  | Control | Treated |
| --- | --- | --- |
| Total number of fat cells ($\times 10^{-6}$) Parametrial | 14.6 ± 3.7 | 8.0 ± 0.6 |

*$p < 0.05$ compared with control

I claim:

1. A method of preventing, controlling or reducing adiposity in animals, comprising administering to said animal an effective amount of a fat cell-specific immunogen which is an antigenic substance selected from the group consisting of plasma membranes of white fat cells of an individual of the same species as said animal or of a species which is closely related phylogenetically to the species of said animal and a fat cell-specific determinant of said plasma membranes, said immunogen being effective to reduce the weight and/or number of fat cells of said animal and thus elicit an immune response in said animal effective to prevent, control or reduce adiposity, and wherein when said animal is meat-producing, subsequently slaughtering said animal for meat.

2. The method according to claim 1, in which said antigenic substance is of an individual of the same species as the animal being treated and modified by conjugation to a carrier which is capable of conferring hapten characteristics upon small molecules.

3. The method according to claim 2, wherein the carrier is a serum albumin.

4. The method according to claim 1, wherein said animal is a lamb, calf or pig.

5. A method of preventing, controlling or reducing adiposity in animals, comprising administering to said animal an effective amount of a fat cell-specific immunogen which is an antigenic substance selected from the group consisting of plasma membranes of white fat cells of an individual of the same species as said animal or of a species which is closely related phylogenetically to the species of said animal and a fat cell-specific determinant of said plasma membranes, said immunogen being effective to reduce the weight and/or number of fat cells of said animal and thus prevent, control or reduce adiposity, said antigenic substance being conjugated to a carrier.

6. The method according to claim 5, wherein the carrier is a serum albumin.

7. The method according to claim 5, wherein said animal is a lamb, calf or pig.

* * * * *